United States Patent
Gharpure et al.

(10) Patent No.: US 11,447,443 B2
(45) Date of Patent: Sep. 20, 2022

(54) PROCESS FOR THE PREPARATION OF DROXIDOPA AND ITS INTERMEDIATE

(71) Applicant: PIRAMAL PHARMA LIMITED, Mumbai (IN)

(72) Inventors: Milind Gharpure, Maharashtra (IN); Ashutosh Jagtap, Maharashtra (IN); Changdev Raut, Maharashtra (IN); Nainesh Kansagara, Maharashtra (IN); Jaisankar Krishnapillai, Tamilnadu (IN); Nirmal Kumar Manoharan, Tamilnadu (IN); Navnath Patil, Maharashtra (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 963 days.

(21) Appl. No.: 16/088,196

(22) PCT Filed: Mar. 28, 2017

(86) PCT No.: PCT/IB2017/051757
§ 371 (c)(1),
(2) Date: Sep. 25, 2018

(87) PCT Pub. No.: WO2017/168313
PCT Pub. Date: Oct. 5, 2017

(65) Prior Publication Data
US 2020/0299227 A1    Sep. 24, 2020

(30) Foreign Application Priority Data
Mar. 30, 2016 (IN) .............................. 201621010969

(51) Int. Cl.
C07C 229/36 (2006.01)
A61K 9/16 (2006.01)
C07F 15/04 (2006.01)

(52) U.S. Cl.
CPC .............. *C07C 229/36* (2013.01); *A61K 9/16* (2013.01); *C07F 15/045* (2013.01)

(58) Field of Classification Search
None
See application file for complete search history.

(56) References Cited

U.S. PATENT DOCUMENTS

| 3,920,728 A | 11/1975 | Hegedüs et al. |
| 4,562,263 A | 12/1985 | Ohashi et al. |
| 8,980,316 B2 | 3/2015 | Ochiai et al. |
| 2009/0074861 A1* | 3/2009 | Ochiai ................ A61K 31/198 424/465 |
| 2013/0253061 A1 | 9/2013 | Pimplaskar et al. |
| 2015/0210667 A1 | 7/2015 | Kandula |

FOREIGN PATENT DOCUMENTS

| EP | 0 024 210 A1 | 8/1980 | |
| WO | 2005/085178 A1 | 9/2005 | |
| WO | WO-2005085178 A1 * | 9/2005 | ........... C07C 227/16 |
| WO | 2013/142093 A1 | 9/2013 | |
| WO | WO-2013142093 A1 * | 9/2013 | ........... C07C 227/18 |

OTHER PUBLICATIONS

McOmie, J. F. W., "Protective Groups in Organic Chemistry", Springer, 1976, ISBN 978-1-4684-72220-2, pp. 130-131, section 3 .2.1. 7 'Cyclic Orthoesters' pp. 130-131.
International Search Report (ISR) for International Application No. PCT/IB2017/051757.
International Search Repor (ISR) for International Application No. PCT/IB2017/051757.
Written Opinion (WO) dated Jun. 1, 2017 for International Application No. PCT/IB2017/051757 dated Jun. 8, 2017
McOmie, J. F. W., "Protective Groups in Organic Chemistry", Springer, 1976, ISBN 978-1-4684-72220-2, pp. 130-131, section 3 .2.1. 7 'Cyclic Orkoesters' pp. 130-131.
Yuri N. Belokon et al.: General Method of Diastereo- and Enantioselective Synthesis of β-Hydroxy-α-amino Acids by Condensation of Aldehydes and Ketones with Glycine J. Am. Chem. Soc. 107. 4252-59 (1985).
Vadim A. Soloshonok, et al: General Method for the Synthesis of Enantiomerically Pure β-Hydroxy-α-amino Acids, containing Fluorine Atoms in the Side Chains. Case of Stereochemical Distinction between Methyl and Trifluoromethyl Groups. X-Ray Crystal and Molecular Structure of the Nickel(ii) Complex of (2S, 3S)-2-(Trifluoro-methyl)threonine: J. Chem. Soc. Perkin Trans. 1, 3143-54 (1993).
Bang-Hua Chen, et al.; Synthesis of 2- and 6-fluoro analogues of threo-3-( 3,4-dihydroxyphenyl) serine (2- and 6-fluoro-threo-DOPS): Journal of Fluorine Chemistry 75, (1995) 93-101.

* cited by examiner

*Primary Examiner* — Dominic Lazaro
(74) *Attorney, Agent, or Firm* — Ladas & Parry LLP

(57) ABSTRACT

The present invention provides an improved process for preparation of L-threo-(2S,3R)-3-(3,4-dihydroxyphenyl)serine (I) (Droxidopa) and its salts; comprising (a) reaction of the aldehyde compound (III) (as described herein) with Metal complex (II) (as described herein), and (h) hydrolysis of the compound (IV) obtained from step (a) in presence of acid. The present invention also relates to a novel intermediates metal chiral complex (IV) for the preparation of Droxidopa.

10 Claims, No Drawings

PROCESS FOR THE PREPARATION OF DROXIDOPA AND ITS INTERMEDIATE

RELATED APPLICATION

This application is a national phase entry under 35 USC 371 of International Patent Application No.: PCT/IB2017/051757 filed on 28 Mar. 2017, which claims priority from Indian Application No. 201621010969 filed on 30 Mar. 2016, the disclosures of which are incorporated in their entirety by reference herein.

FIELD OF THE INVENTION

The present invention relates to an improved process for the preparation of L-threo-(2S,3R)-3-(3.4-dihydroxyphenyl) serine (I), which is known as Droxidopa and its pharmaceutically acceptable salts. The present invention also relates to a novel metal chiral complex (IV) as an intermediate used for the preparation of droxidopa.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

Droxidopa is chemically known as (2S,3R)-2-amino-3-(3,4-dihydroxyphenyl)-3-hydroxypropanoic acid and it is structurally represented by the following formula (I). It is also known as L-threo-(2S,3R)-3-(3,4-dihydroxyphenyl)serine. Droxidopa is available in the market as Northera® capsules with dosages of 100 mg, 200 mg and 300 mg for oral administration.

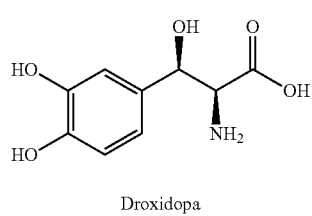

Droxidopa (I)

NORTHERA® (droxidopa) capsules, for oral use is approved in the USA and is indicated for the treatment of orthostatic dizziness, light headedness, or the "feeling that you are about to black out" in adult patients with symptomatic neurogenic orthostatic hypotension caused by primary autonomic failure, dopamine beta-hydroxylase deficiency, and non-diabetic autonomic neuropathy. Droxidopa is a synthetic amino acid analog that is directly metabolized to norepinephrine by dopadecarboxylase, which is extensively distributed throughout the body.

The drug was originally launched in 1989 in Japan by Sumitomo Dainippon Pharma for the oral treatment of frozen gait or dizziness associated with Parkinson's disease and for the treatment of orthostatic hypotension, syncope or dizziness associated with Shy-Drager syndrome and familial amyloidotic polyneuropathy.

Chirality has acquired increasing importance for the pharmaceutical industry, as evidenced by the fact that more than 80% of the drugs developed hitherto have chiral properties. The various enantiomers may develop completely different effects in the body, so that only one of two or more enantiomeric forms administered may be effective. In the case of Droxidopa (I), it has been observed that the L-threo enantiomer is the desired isomer having desired activity. Administration of the active L-threo enantiomer of the compound (I), substantially free of its other isomers, would essentially enable a reduction in the dose of drug. Due to the importance of the L-threo enantiomer of the compound (I) as an oral, synthetic norepinephrine precursor, there exists a need to develop an economical and efficient synthetic process for its production.

U.S. Pat. No. 3,920,728 (hereinafter US'728) provides a process for the preparation of droxidopa comprising reaction of 3,4-dibenzyloxybenzaldehyde with glycine, followed by treatment with sodium acetate trihydrate and diethylamine to obtain racemic-threo/erythro-3-(3,4-dibenzyloxyphenyl)-serine. Further, treatment of the compound with carbobenzoxy chloride to obtain racemic-threo/erythro-3-(3,4-dibenzyloxyphenyl)-N-carbobenzoxyserine and its treatment with dicyclohexylamine to give racemic-threo-3-(3,4-dibenzyloxyphenyl)-N-carbobenzox yserinedic yclohexylamine salt, which on treatment with HCl gas in the presence of ethyl acetate yields racemic-threo-3-(3,4-dibenzyloxyphenyl)-N-carbobenzoxyserine. Finally, treatment of the racemic serine compound with (+)-ephedrine to yield (+)-ephedrine salt of L-threo-3-(3,4-dibenzyloxyphenyl)-N-carbobenzoxyserine and hydrolysis of the compound to yield L-threo-3-(3,4-dibenzyloxyphenyl)-N-carbobenzoxyserine; which on subsequent reduction over Pd/C provides L-threo-3-(3,4-dibenzyloxyphenyl)-serine.

The patent EP0024210B1 describes a process for preparation of optically active (D- or L-) threo-3-(3,4-dihydroxyphenyl)serine (Droxidopa) comprising reaction of racemic threo-3-(3,4-dibenzyloxyphenyl)-N-carbobenzoxyserine with a resolving agent, followed by decomposition using hydrochloric acid to yield (−)-3-(3,4-dibenzyloxyphenyl)-N-carbobenzoxyserine.

U.S. Pat. No. 4,562,263 (hereinafter US'263) discloses a process for preparation of droxidopa comprising optical resolution of N-phthaloyl-3-(3,4-methylenedioxyphenyl) serine using optically active amine selected from the group consisting of strychinine, cinconidine, L-norephedrine, S-2-amino-1,1-diphenyl-1-propanol and L-3-hydroxy-3-(4-nitrophenyl)-2-amino-1-propanol to yield L-N-phthaloyl-3-(3, 4-methylenedioxyphenyl)serine, reacting the resulting compound with a Lewis acid selected from the group consisting of aluminium trichloride, aluminium tribromide, boron trichloride and boron tribromide to form N-phthaloyl-3-(3,4-dihydroxyphenyl)-serine; which on further deprotection by removal of phthaloyl group with hydrazine to yield L-threo-3-(3,4-dihydroxyphenyl)-serine.

Research article *J. Am. Chem. Soc.* 107, 4252-59 (1985) disclosed a 'general method of Diastereo- and Enantioselective Synthesis of beta-Hydroxy-alpha-amino acids by condensation of aldehydes and ketones with Glycine' which involves formation of metal complex as:

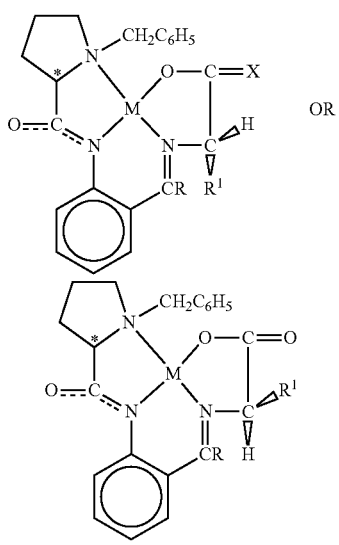

The *J. Am. Chem. Soc.* 107, 4252-59 (1985) further disclosed hydrolysis of the metal complex to give desired compound.

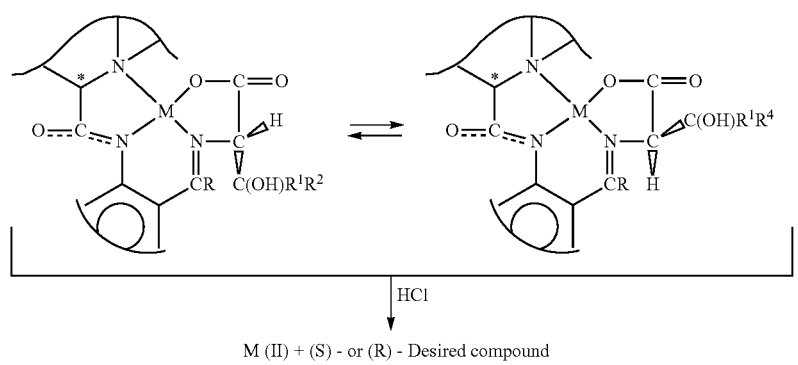

Similarly, Journal of fluorine chemistry 75, 93-101, (1995) refers to the synthesis of 2- and 6-fluoro analogues of threo-3-(3,4-dihydroxyphenyl) serine (2- and 6-fluoro-threo-DOPS) comprises treatment of aldehyde compound with $Ni^{++}$ followed by hydrolysis which is depicted below;

((S-8))

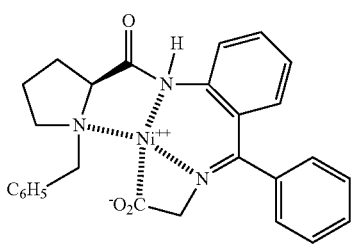

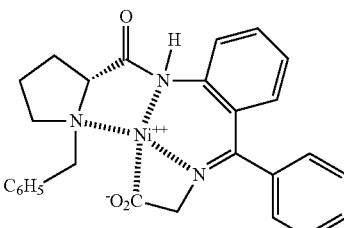

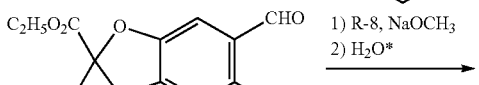

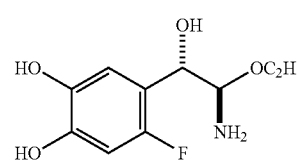

The published PCT application WO-A-2005/085178 disclosed the treatment of 1-hydroxy-1-(3,4-dibenzyloxyphenyl) glycine-Ni-D-2-[N—(N'-ben-zylprolyl) amino] benzophenone with hydrochloric acid to obtain L-threo-(2S,3R)-3-(3,4-dibenzyloxyphenyl) serine. As indicated, the said compound has both the hydroxyl group protected with benzyl group forms 3,4-dibenzyloxyphenyl compound. The product on subsequent metal catalyzed hydrogenation, predominately using Pd/C under hydrogenation pressure provides Droxidopa.

A general method for the synthesis of enantiomerically pure beta-Hydroxy-alpha-amino acids and serine derivatives is also disclosed in the *J. Chem. Soc. Perkin Trans.* 1, 3143-54 (1993) and published patent application US 2015/0210667A1. U.S. Pat. No. 8,980,316 (hereinafter US'316) and published patent application US 2013/0253061A1 disclosed a composition of Droxidopa with several particle size rages in terms of 90% D (μm) values and average (μm) values.

It is evident from the above discussion that the prior art processes for the preparation of droxidopa involves multiple process steps such as resolution followed by separate deprotection method. The use of resolving agent renders the process costly. Partial recycling of the resolving agent is feasible but such recycling is costly as it requires additional processing and is also associated with waste generation. The undesired enantiomer cannot be recycled and is discarded.

The chiral resolution to obtain threo/erythro isomer results into 50% loss of the undesired isomer, which affects the overall yield of the process. Further, the process involves use of complex agents for isomer separation, which also results in <50% of desired isomer. Also, the hydrazine used for the deprotection of phthaloyl group is known to be genotoxic, and thus it is required to remove traces of hydrazine from the final product, droxidopa.

Thus, in view of these drawbacks there is a need to develop an alternative asymmetric synthesis which would provide the desired L-threo isomer in an efficient and more specific manner. The said prior art processes are therefore disadvantageous for commercial manufacturing due to non-feasibility of the reaction process owing to use of genotoxic reagents, and due to the elaborate and tedious nature of the process, providing low yield of the desired isomer.

Inventors of the present invention have developed an improved process which is a simple, efficient and cost-effective process and provides the desired compounds in improved yield and purity and that addresses the problems associated with the processes reported in the prior art. The process of the present invention does not involve use of any toxic and/or costly solvents, also does not involve use of costlier coupling agents and reagents. Moreover, the process does not require repetitive purification steps and column chromatography. Accordingly, the present invention provides a process for the preparation of droxidopa (I), which is simple, efficient, cost effective, environmentally friendly and commercially scalable for large scale operations.

SUMMARY OF THE INVENTION

In one aspect, the present invention relates to an improved process for the preparation of L-threo-(2S,3R)-3-(3,4-dihydroxyphenyl)serine (I) or a salt thereof; comprising (a) reaction of the aldehyde compound (III) (as described herein) with Metal complex (II) (as described herein), and (b) hydrolysis of the compound (IV) obtained from step (a) in presence of acid.

In one aspect, the present invention relates to an improved process for the preparation of L-threo-(2S,3R)-3-(3,4-dihydroxyphenyl)serine (I) or a salt thereof; comprising reaction of the aldehyde compound (III) (as described herein) with Metal complex (II) (as described herein) in the presence of a metal alkoxide to obtain compound (IV), followed by its hydrolysis in presence of acid.

In an embodiment, there is provided a novel intermediate metal complex (IV);

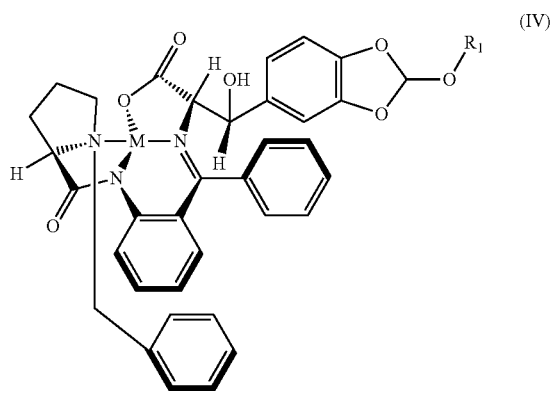

wherein M is a metal selected from $Cu^{2+}$, $Ni^{2+}$, or $Zn^{2+}$ and $R_1$ is selected from a group consisting of hydrogen, unsubstituted or substituted alkyl, cycloalkyl, aryl, heterocyclic and protecting group;

In an embodiment, there is provided a novel intermediate Nickel complex (IVa);

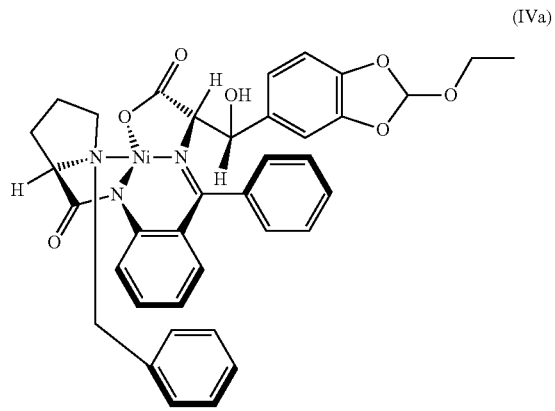

In another aspect, the present invention relates to an improved process for the preparation of L-threo-(2S,3R)-3-(3,4-dihydroxyphenyl)serine (I) or a salt thereof comprising (i) reaction of the aldehyde compound (IIIa) (as described herein) with Nickel complex (IIa) (as described herein), (ii) hydrolysis of the compound (IVa) obtained from step (i) in presence of acid, and (iii) treatment of the acid salt of compound (I) obtained from step (ii) with a base.

In one aspect, the present invention relates to an improved process for the preparation of L-threo-(2S,3R)-3-(3,4-dihydroxyphenyl)serine (I) or a salt thereof; comprising hydrolysis of the compound (IV) (as described herein) in presence of acid.

In an embodiment, there is provided L-threo-(2S,3R)-3-(3,4-dihydroxyphenyl)serine (I) with more than 99% ee.

In another aspect, the invention also provides a process for the purification of L-threo-(2S,3R)-3-(3,4-dihydroxyphenyl)serine (I) comprising treatment of compound (I) or its salt with a metal hydride.

In another aspect, there is provided L-threo-(2S,3R)-3-(3,4-dihydroxyphenyl)serine (I) having particle size diameter range with a d(0.1) of between about 1 to about 20 μm.

In another aspect, there is provided L-threo-(2S,3R)-3-(3,4-dihydroxyphenyl)serine (I) having particle size diameter range with a d(0.5) of between about 5 to about 105 μm.

In another aspect, there is provided L-threo-(2S,3R)-3-(3,4-dihydroxyphenyl)serine (I) having particle size diameter range with a d(0.9) of between about 10 to about 210 μm.

In another aspect, there is provided a pharmaceutical composition comprising a therapeutically effective amount of L-threo-(2S,3R)-3-(3,4-dihydroxyphenyl)serine (I) having particle size distribution range of d(0.1) between about 1 to about 20 μm, d(0.5) between about 5 to about 105 μm, d(0.9) between about 10 to about 210 μm; or any combination thereof.

In another aspect, there is provided L-threo-(2S,3R)-3-(3,4-dihydroxyphenyl)serine (I) having specific surface area value from 0.1 to 3 $m^2/g$.

DETAILED DESCRIPTION OF THE INVENTION

Accordingly, the present invention relates to an improved process for the preparation of L-threo-(2S,3R)-3-(3,4-dihydroxyphenyl)serine (I) or a salt thereof represented by the following formula,

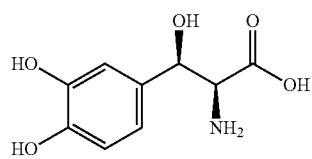

comprising the steps of,
(a) preparation of metal complex (IV) represented by the following formula,

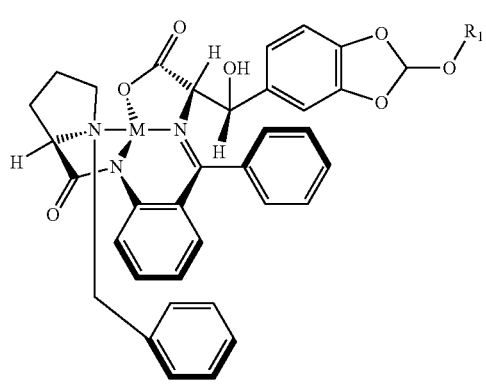

wherein M is a metal selected from $Cu^{2+}$, $Ni^{2+}$, or $Zn^{2+}$ by reacting the aldehyde (III) represented by the following formula,

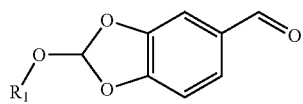

wherein $R_1$ is selected from a group consisting of hydrogen, unsubstituted or substituted alkyl, cycloalkyl, aryl, heterocyclic and protecting group;
with Metal complex (II) represented by the following formula,

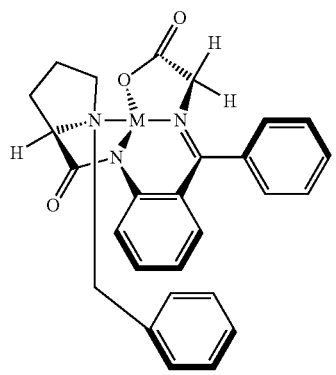

in the presence of a metal alkoxide; and
(b) hydrolyzing of the compound (IV) obtained from step (a) in presence of acid.

In the context of the present invention, the term 'hydrolysis' used in reference to any step of the reaction corresponds to the decomposition of metal complex (IV) and subsequent deprotection of the methylene dioxy group to yield dihydroxy compound of formula (I).

Accordingly, in the process of the present invention the intermediate metal complex compound (IV) is optionally isolated during reaction, or in-situ converted to the compound (I) or its salt.

In an embodiment the 'metal alkoxide' is selected from the group consisting of sodium methoxide, sodium ethoxide, sodium isopropoxide, potassium methoxide, sodium tertiary butoxide, potassium tertiary butoxide, or mixtures thereof.

In an embodiment the 'acid' is selected from the group consisting of hydrochloric acid (HCl), hydrobromic acid, hydrofluoric acid, nitric acid, sulfuric acid and phosphoric acid or mixtures thereof.

In accordance with the embodiments of the present invention, the unsubstituted or substituted alkyl is $(C_1-C_{10})$-alkyl, which may be a straight-chain or branched chain alkyl; for example, $C_1-C_{10}$ for straight chain and $C_3-C_{10}$ for branched chain. Suitable alkyl groups containing from one to ten carbon atoms, include, but are not limited to, methyl, ethyl, n-propyl, isopropyl, n-butyl, t-butyl, iso-butyl, sec-butyl, n-pentyl, isopentyl, 2-pentyl, 3-pentyl, neo-pentyl, n-hexyl, isohexyl, 2-hexyl, 3-hexyl, n-heptyl, isoheptyl, 2-heptyl, 3-heptyl, n-octyl, isooctyl, 2-octyl, 3-octyl, n-nonyl, isononyl, 2-nonyl, 3-nonyl, n-decyl, isodecyl, 2-decyl and 3-decyl.

Furthermore, the alkyl groups may be unsubstituted or substituted with one or more substituents. A substituted alkyl refers to a $(C_1-C_{10})$-alkyl substituted with one or more groups, preferably 1-3 groups, independently selected from halogen, hydroxy, $(C_1-C_6)$-alkoxy, nitro, cyano, amino, substituted amines, C(O) and $C(O)_2$-alkyl.

In accordance with the embodiments of the present invention, the cycloalkyl is $(C_1-C_{12})$-cycloalkyl, wherein a saturated or partially unsaturated cyclic hydrocarbon radical including 1, 2 or 3 rings and including a total of 3 to 12 carbon atoms forming the rings. The term cycloalkyl includes bridged, fused and spiro ring systems. Examples of cycloalkyl include, but are not limited to, cyclopropyl, cyclobutyl, cyclopentyl, cyclohexyl, adamantyl, norbornyl, bicyclo[2.1.0]pentane, bicyclo[2.2.1]heptyl, bicyclo[2.2.1]hept-2-ene, spiro[3.3]heptanes and 1,2,3,3a-tetrahydropentalene.

Furthermore, the cycloalkyl group may be unsubstituted or substituted with one or more groups, preferably 1-3 groups independently selected from halogen, hydroxy, $(C_1-C_6)$-alkoxy, nitro, cyano, amino, substituted amines, C(O) and $C(O)_2$-alkyl.

In accordance with the embodiments of the present invention, the aryl is $(C_6-C_{14})$-aryl, which refers to monocyclic or bicyclic hydrocarbon groups having 6 to 14 ring carbon atoms, preferably 6 to 10 carbon atoms in which the carbocyclic ring(s) present have a conjugated pi electron system. Examples of $(C_6-C_{14})$-aryl residues are phenyl, naphthyl, fluorenyl and anthracenyl. Aryl groups can be unsubstituted or substituted with one or more groups, for example 1, 2, 3, 4 or 5 groups independently selected from halogen, hydroxy, ($C_1$-$C_6$)-alkoxy, nitro, cyano, amino, substituted amines, $C(O)$ and $C(O)_2$-alkyl.

In accordance with the embodiments of the present invention, the heterocyclic is a 3- to 9-membered saturated or partially unsaturated monocyclic or bicyclic ring system containing one to four identical or different hetero atoms selected from a nitrogen (N), a sulphur (S) or an oxygen (O) atom. Heterocyclyl includes saturated heterocyclic ring systems, which do not contain any double bond. Partially unsaturated heterocyclic ring systems containing at least one double bond, but do not form an aromatic system containing hetero atom. Suitable saturated and partially unsaturated heterocyclic groups include, but are not limited to, aziridine, oxirane, oxiridine, thiirane, oxetane, azetidine, thietane, tetrahydrofuran, tetrahydrothiophene, pyrrolidine, dihydropyran, tetrahydropyran, thio-dihydropyran, thio-tetrahydropyran, piperidine, piperazine, morpholine, 1,3-oxazinane, 1,3-thiazinane, 4,5,6-tetra hydropyrimidine, 2,3-dihydrofuran, dihydrothiene, dihydropyridine, tetrahydro pyridine, isoxazolidine, pyrazolidine, azepane, oxepane, thiepane and azocane.

Further, the heterocyclic having an aromatic ring containing heteroatom/s are herein referred to by the customary term "heteroaryl". Within the context of the present invention and as used herein, the term "heteroaryl" refers to a 5 to 10-membered aromatic monocyclic or bicyclic ring system containing one to four identical or different hetero atoms selected from N, S or an O atom. Examples of heteroaryl include, but are not limited to pyrrole, pyrazole, imidazole, triazole, pyrazine, furan, thiophene, oxazole, thiazole, benzimidazole, benzoxazole, benzothiazole, benzofuran, indole, indazole, isoindole, isoquinoline, isooxazole, triazine, purine, pyridine, quinoline, oxadiazole, thiene, pyridazine, pyrimidine, isothiazole, quinoxaline (benzopyrazine), tetrazole, azepine, oxepine, thiepine and azocine. The oxidized form of the ring nitrogen atom of the heteroaryl to provide N-oxide is also encompassed.

Furthermore, the heterocyclic group may be unsubstituted or substituted with one or more groups, preferably 1-3 groups independently selected from halogen, hydroxy, ($C_1$-$C_6$)-alkoxy, nitro, cyano, amino, substituted amines, $C(O)$ and $C(O)_2$-alkyl.

In accordance with the embodiments of the present invention, the 'protecting group' is an hydroxyl protecting group which refers to the group tosyl, mesyl, nosyl, acetyl, benzoyl, substituted benzoyl, benzyl, substituted benzyl, dimethoxy trityl, methoxy trityl, and the like.

Accordingly, in an embodiment the present invention relates to an improved process for the preparation of L-threo-(2S,3R)-3-(3,4-dihydroxyphenyl)serine (I) represented by the following formula,

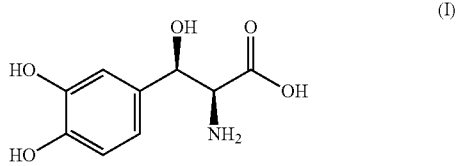 [SMILES: N[C@H](C(=O)O)[C@H](O)c1ccc(O)c(O)c1]

comprising the steps of,
(i) preparation of metal complex (IVa) represented by the following formula,

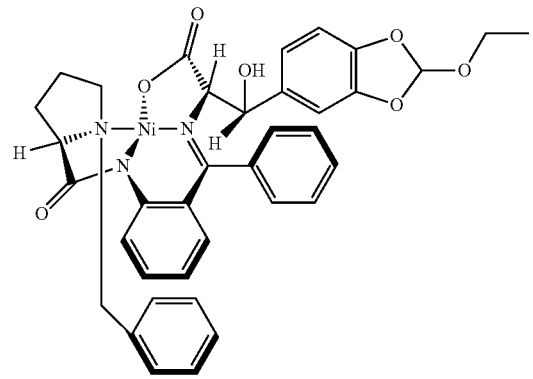

by reacting the 2-ethoxybenzo[d][1,3]dioxole-5-carbaldehyde (IIIa) represented by the following formula,

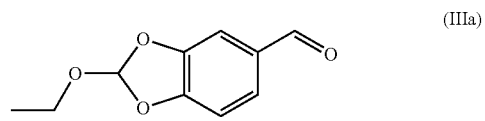

with Metal complex (IIa) represented by the following formula,

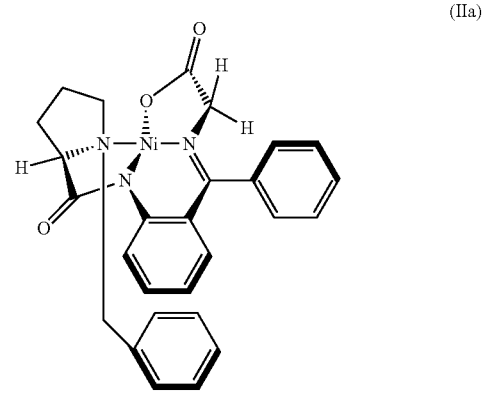

in the presence of sodium methoxide;
(ii) hydrolysis of the compound (IVa) obtained from step (i) in presence of acid to obtain salt of compound (I) represented by the following formula,

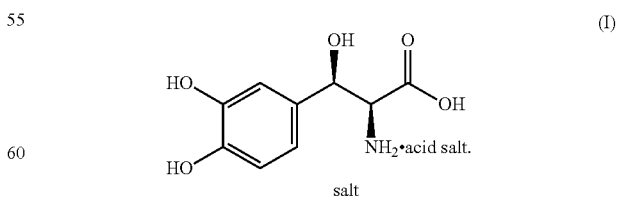

(iii) treatment of the acid salt of compound (I) obtained from step (ii) with a base.
In an embodiment, the acid is hydrochloric acid.
In an embodiment, the base is triethylamine.

In a specific embodiment, the process for the preparation of L-threo-(2S,3R)-3-(3,4-dihydroxyphenyl)serine (I) comprises the steps of;
(1) adding the compound (III) in a solvent,
(2) adding metal alkoxide and the compound (II) to the reaction mixture of step (1),
(3) optionally isolating the compound (IV),
(4) adding an acid to the stirring solution containing compound (IV),
(5) optionally isolating salt of compound (I) of step (4),
(6) adding a base to the stirring solution containing salt of compound (I),
(7) isolating the desired product.

The process of the present invention as per the specific embodiment described above is illustrated in the following Scheme (I), solvent such as toluene, xylene and benzene; acetone; water or a mixture thereof The metal alkoxide used in the step (2) of the above process (as depicted in the Scheme (I)) is selected from the sodium methoxide, sodium ethoxide, sodium isopropoxide, potassium methoxide, sodium tertiary butoxide, potassium tertiary butoxide, or mixtures thereof.

The term 'isolating' referred to in the step (3), step (5) and step (7) of the above process (as depicted in the Scheme (I)) corresponds to the steps involving biphasic separation, separation of organic phase, filtration, evaporation of solvent, cooling, precipitation, washing and/or drying.

The acid used in the step (4) of the above process (as depicted in the Scheme (I)) is selected from hydrochloric

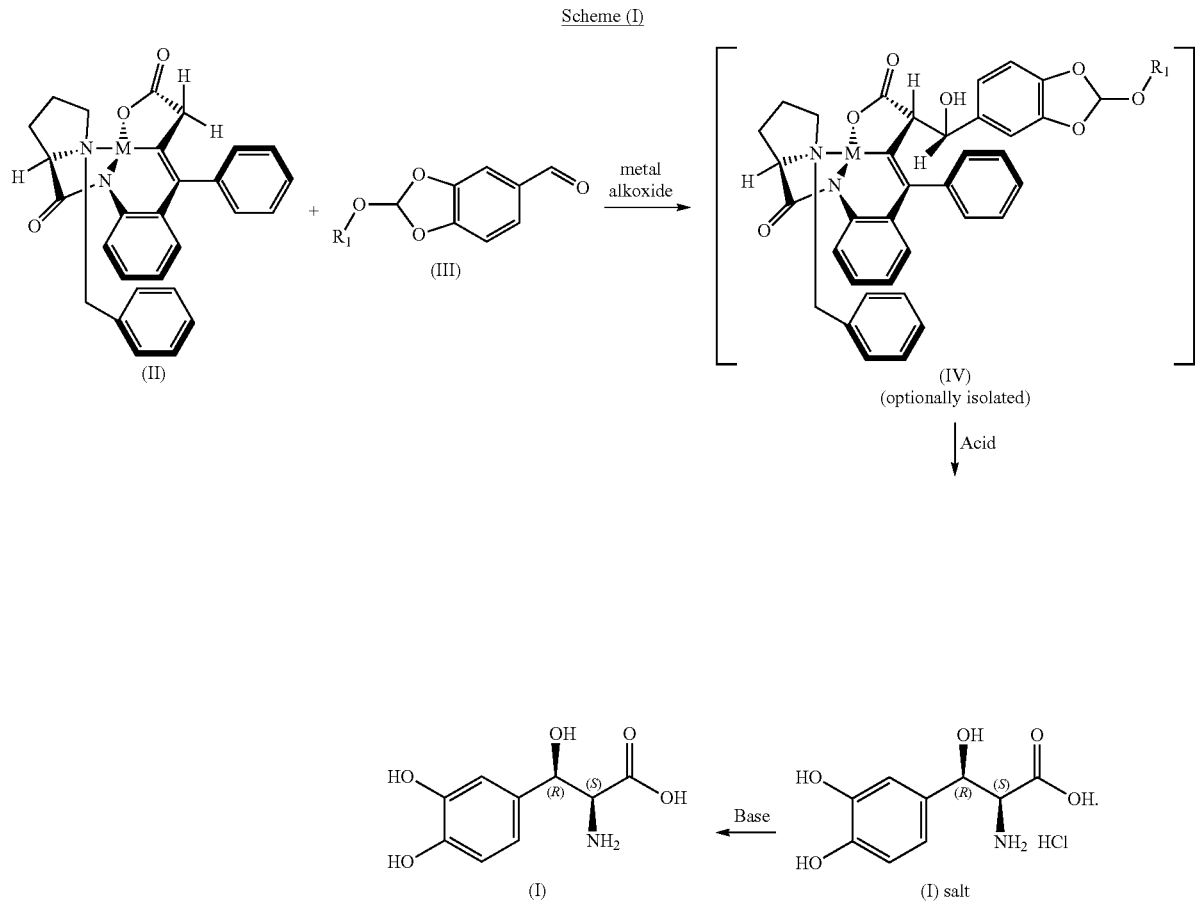

The solvent used in the step (1) to step (7) of the above process (as depicted in the Scheme-I) is selected from a halogenated solvent such as dichloromethane, 4-bromotoluene, diiodomethane, carbon tetrachloride, chlorobenzene and chloroform; alcoholic solvent such as methanol, ethanol, isopropanol, t-amyl alcohol, t-butyl alcohol and hexanol; an ether solvent such as tetrahydrofuran, cyclopentyl methyl ether, 2-methyltetrahydrofuran, diethyl ether and 1,4-dioxane; a ketone selected from methyl ethyl ketone, acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic acid, hydrobromic acid, hydrofluoric acid, nitric acid, sulfuric acid and phosphoric acid or mixtures thereof.

The base used in the step (6) of the above process (as depicted in the Scheme (I)) is selected from an organic base or an inorganic base such as triethylamine (TEA), N,N-diisopropylethylamine, tripropylamine, pyridine, sodium carbonate, sodium bicarbonate, potassium carbonate, sodium hydroxide, potassium hydroxide, lithium hydroxide, lithium carbonate, sodium bicarbonate, potassium bicarbonate, sodium hydride, or a mixture thereof.

The overall process of the present invention involving preparation of droxidopa (I) via formation of intermediate compound (IVa) is illustrated in the following Scheme (II):

Scheme (II)

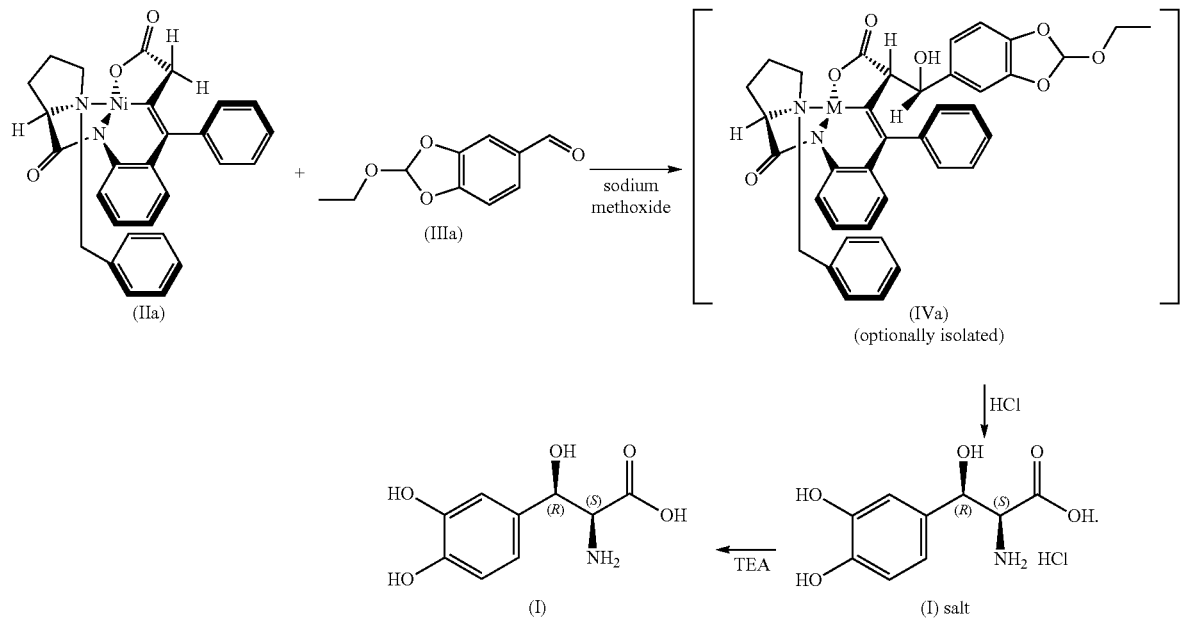

The process illustrated in the above scheme (II) comprises reaction of the compound (IIa) with 2-ethoxybenzo[d][1,3] dioxole-5-carbaldehyde (IIIa) in the presence of a metal alkoxide selected from sodium methoxide to obtain compound (IVa) which is optionally isolated or in-situ hydrolysed by the treatment with an acid selected from hydrochloric acid to obtain salt of droxidopa (I). The salt was treated with a base selected from triethylamine in aqueous medium and the desired product was obtained with more than 99% ee.

In an embodiment, there is provided L-threo-(2S,3R)-3-(3,4-dihydroxyphenyl)serine (I) with Nickel (Ni) content less than 30 ppm.

In an embodiment, there is provided L-threo-(2S,3R)-3-(3,4-dihydroxyphenyl)serine (I) with Nickel (Ni) content less than 20 ppm.

In an embodiment, there is provided L-threo-(2S,3R)-3-(3,4-dihydroxyphenyl)serine (I) with Nickel (Ni) content less than 10 ppm.

The inventors of the process of the instan invention observed that the elemental impurity content of the final product (Droxidopa) obtained by this process is very low and does not require any specific purification technology to remove elemental impurities such Nickel (Ni).

The following Table-1 indicated Nickel content in the final product (Droxidopa) obtained by the process of the instant invention:

TABLE 1

| Sample | Parameter | Result (Ni content) |
| --- | --- | --- |
| Sample 1 | Nickel by ICP | 7.521 ppm |
| Sample 2 | Nickel by ICP | 3.711 ppm |
| Sample 3 | Nickel by ICP | 12.11 ppm |
| Sample 4 | Nickel by ICP | 19.75 ppm |

Accordingly, it is also evident that the product Droxidopa (I) obtained by the process of the instant invention has a high enantiomeric excess (ee).

In an another embodiment, there is provided L-threo-(2S, 3R)-3-(3,4-dihydroxyphenyl)serine (I) with more than 99% ee.

In an another embodiment, there is provided L-threo-(2S, 3R)-3-(3,4-dihydroxyphenyl)serine (I) with more than 99.5% ee.

In an another embodiment, there is provided L-threo-(2S, 3R)-3-(3,4-dihydroxyphenyl)serine (I) with more than 99.99% ee.

In an embodiment, there is provided a novel intermediate metal complex (IV);

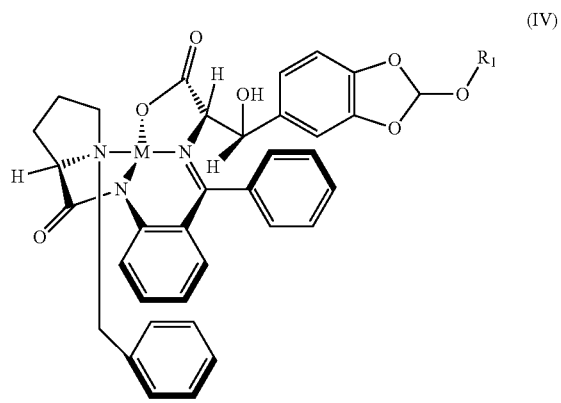

wherein; M is a metal selected from $Cu^{2+}$, $Ni^{2+}$, or $Zn^{2+}$; and $R_1$ is selected from a group consisting of hydrogen, unsubstituted or substituted alkyl, cycloalkyl, aryl, heterocyclic and protecting group.

In an embodiment, there is provided a novel intermediate Nickel complex (IVa);

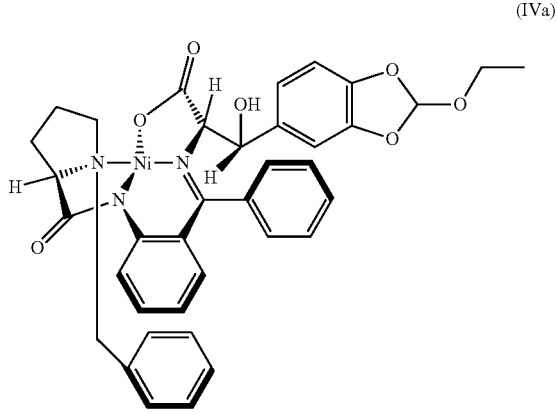

(IVa)

Accordingly in yet another aspect, the present invention relates to an improved process for the preparation of L-threo-(2S,3R)-3-(3,4-dihydroxyphenyl)serine (I) or a salt thereof represented by the following formula,

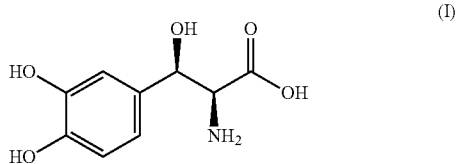 [SMILES: N[C@H](C(=O)O)[C@H](O)c1ccc(O)c(O)c1]

(I)

comprising hydrolysis of the compound (IV) represented by the following formula,

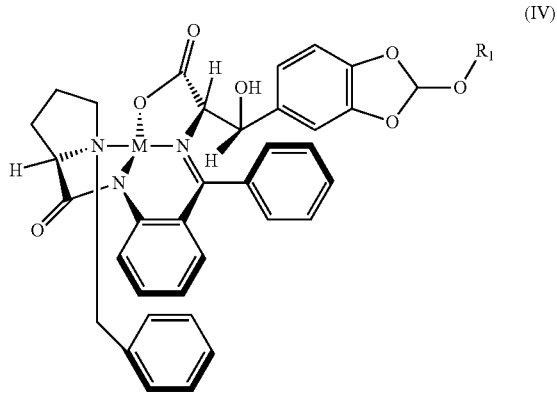

(IV)

wherein M and $R_1$ are as defined above; in the presence of an acid.

In another aspect, the invention also provides a process for the purification of L-threo-(2S,3R)-3-(3,4-dihydroxyphenyl)serine (I) comprising treatment of compound (I) or its salt with a metal hydride.

In an embodiment, there is provided a method for the purification of Droxidopa (I) or its salts using a metal hydride.

In an another specific embodiment, the process for the preparation of pure L-threo-(2S,3R)-3-(3,4-dihydroxyphenyl)serine (I) having total impurity less than 0.06% comprises the steps of;
(p) adding Droxidopa (I) salt to a solvent,
(q) adding a metal hydride to the stirring solution of step (p),
(r) isolating pure Droxidopa (I) salt or its free base.

In an embodiment, the solvent used in the step (p) of the above process is selected from water; a halogenated solvent such as dichloromethane, 4-bromotoluene, diiodomethane, carbon tetrachloride, chlorobenzene and chloroform; alcoholic solvent such as methanol, ethanol, isopropanol, t-amyl alcohol, t-butyl alcohol and hexanol; an ether solvent such as tetrahydrofuran, cyclopentyl methyl ether, 2-methyltetrahydrofuran, diethyl ether and 1,4-dioxane; a ketone selected from methyl ethyl ketone, acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; acetone; or a mixture thereof.

In an embodiment, the metal hydride used in the step (q) of the above process is selected from boron hydride, lithium borohydride, sodium borohydride, potassium borohydride, sodium cyanoborohydride, sodium dialkylamine borohydride, dialkyl aluminum hydride, aluminum hydride, sodium aluminum hydride, lithium aluminum hydride, sodium hydride, potassium hydride, rubidium hydride and cesium hydride or mixture thereof.

As illustration, the purification process comprises, dissolving the Droxidopa (I) hydrochloride salt (35 g) in the demineralized water followed by the addition of concentrated HCl and further dropwise addition of 0.1% w/w sodium borohydride solution in 4 volumes (V) of demineralized (DM) water (with respect to weight of HCl salt). The reaction mixture was filtered, treated with activated carbon and passed through Hyflo® bed to provide the pure aqueous solution of L-threo-(2S,3R)-3-(3.4-dihydroxyphenyl)serine (I) hydrochloride with impurity less than 0.06%; which is further treated with a base to obtain its free base that is pure L-threo-(2S,3R)-3-(3.4-dihydroxyphenyl)serine (I) (Droxidopa).

The inventors of the process of the instant invention observed that the total impurity content of the Droxidopa obtained by this process is very low as less than 0.06%.

The following Table-2 indicated impurity content in the final product (Droxidopa) obtained by the process of the instant invention:

TABLE 2

| Sample | HPLC purity |
| --- | --- |
| Sample 1 | 99.9%, any individual known impurity 0.04% |
| Sample 2 | 99.8%, any individual known impurity 0.04% |
| Sample 3 | 99.9%, any individual known impurity 0.05% |
| Sample 4 | 99.9%, any individual known impurity 0.05% |

In another aspect, there is provided L-threo-(2S,3R)-3-(3,4-dihydroxyphenyl)serine (I) having particle size diameter range with a d(0.1) of between about 1 to about 20 μm.

In another aspect, there is provided L-threo-(2S,3R)-3-(3,4-dihydroxyphenyl)serine (I) having particle size diameter range with a d(0.5) of between about 5 to about 105 μm.

In another aspect, there is provided L-threo-(2S,3R)-3-(3,4-dihydroxyphenyl)serine (I) having particle size diameter range with a d(0.9) of between about 10 to about 210 μm.

The following Table-3 indicates the particle size range of Droxidopa (I) as observed by the inventors:

TABLE 3

|  | Before milling | After milling |
| --- | --- | --- |
| Droxidopa particle size d(0.1) μm | 9.49 | 3.02 |
|  | 18.33 | 2.37 |
|  | 5.4 | 2.08 |
| Droxidopa particle size d(0.5) μm | 54.77 | 14.25 |
|  | 103.87 | 5.93 |
|  | 38.3 | 9.52 |
| Droxidopa particle size d(0.9) μm | 190.7 | 57.78 |
|  | 207.5 | 12.55 |
|  | 97.3 | 29.15 |

The above particle size ranges were observed when measured by Malvern Mastersizer particle size analyzer equipped with a 30 mm lens Mastersizer 2000, SCIROCCO 2000, air compressor and vacuum pump. In general, the particle size distribution may be achieved by the process of the present invention or alternatively by any one of the known methods reported in the art like milling, micronization, grinding or sieving, which may reduce the particle.

Accordingly, there is provided L-threo-(2S,3R)-3-(3,4-dihydroxyphenyl)serine (I) having a particle size diameter range with a d(0.1) of between about 5 to about 20 μm, before milling.

Accordingly, there is provided L-threo-(2S,3R)-3-(3,4-dihydroxyphenyl)serine (I) having a particle size diameter range with a d(0.1) of between about 1 to about 5 μm, after milling.

Accordingly, there is provided L-threo-(2S,3R)-3-(3,4-dihydroxyphenyl)serine (I) having a particle size diameter range with a d(0.5) of between about 35 to about 105 μm, before milling.

Accordingly, there is provided L-threo-(2S,3R)-3-(3,4-dihydroxyphenyl)serine (I) having a particle size diameter range with a d(0.5) of between about 5 to about 15 μm, after milling.

Accordingly, there is provided L-threo-(2S,3R)-3-(3,4-dihydroxyphenyl)serine (I) having a particle size diameter range with a d(0.9) of between about 95 to about 210 μm, before milling.

Accordingly, there is provided L-threo-(2S,3R)-3-(3,4-dihydroxyphenyl)serine (I) having a particle size diameter range with a d(0.9) of between about 10 to about 60 μm, after milling.

In another aspect, there is provided a pharmaceutical composition comprising a therapeutically effective amount of L-threo-(2S,3R)-3-(3,4-dihydroxyphenyl)serine (I) having particle size distribution range of d(0.1) between about 1 to about 20 μm, d(0.5) between about 5 to about 105 μm, d(0.9) between about 10 to about 210 μm; or any combination thereof.

In another aspect, there is provided L-threo-(2S,3R)-3-(3,4-dihydroxyphenyl)serine (I) having specific surface area value from 0.1 to 3 m$^2$/g.

In an embodiment, there is provided L-threo-(2S,3R)-3-(3,4-dihydroxyphenyl)serine (I) having surface area BET gas absorption value of from 0.1 to 3 m$^2$/g; preferably from 0.12 to 2 m$^2$/g; more preferably from 0.14 to 1.5 m$^2$/g.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1: Preparation of Nickel Complex (IVa)

Charged 300 mL of methanol in a flask followed by the addition of Nickel complex (IIa) (100 g) at temperature of about 25-30° C. To the stirring solution was added 120 mL of 25% Sodium methoxide solution and (40.9 g) aldehyde compound (IIIa). The reaction mixture was stirred for about 1 hour and quenched in acetic acid: water mixture (200 mL of 20% acetic acid & 1000 mL of demineralized (DM) water). The reaction mixture was filtered and solid washed with 300 mL of DM water. The residue was treated with (600 mL) to obtain desired product (HPLC purity: 83.4%)

Example-2: Preparation of L-threo-(2S,3R)-3-(3.4-dihydroxyphenyl)serine (I)

Charged 300 mL of methanol in a flask followed by the addition of Nickel complex (IVa) (30 g) at temperature of about 25-30° C. To the stirring solution was added (75 mL) of 5N HCl and the reaction mixture was heated to 40° C. After 2 hours, the reaction was cooled to 25-30° C. and concentrated under vacuum. The residue of crude Droxidopa hydrochloride salt was converted to its free base by adjusting the pH to 7.5-8.5 with 25% triethylamine in methanol solution in 5 volumes (V) (w.r.t weight. of HCl salt) DM water medium for about 1 hour. The solid was filtered and washed with (2×4V) of DM water and (2×7V) of methanol to obtain desired product. (Yield 76%, chiral purity 99.65% (ee)).

Example-3: Preparation of L-threo-(2S,3R)-3-(3.4-dihydroxyphenyl)serine (I) Hydrochloride Charged 420 mL of methanol in a flask followed by the addition of sodium methoxide solution (55 mL), Nickel complex (IIa) (100 g) and aldehyde compound (IIIa). The reaction mixture was stirred at temperature of about 15-20° C. for about 1 hour. The reaction mixture was further cooled to about 10° C. temperature; to the reaction mixture was added concentrated hydrochloric acid (100 mL) and stirred for 3 hours at elevated temperature of about 40° C. The reaction mixture was filtered and washed with aqueous HCl. The aqueous filtrate was separately treated with methylene dichloride (350 mL) and ethyl acetate (350 mL) respectively. The separated aqueous layer was cooled to −5-5° C. of temperature and stirred for about 3 hour to obtain solid precipitate of L-threo-(2S,3R)-3-(3.4-dihydroxyphenyl)serine (I) HCl salt. The obtained (I) HCl salt was recrystallized from isopropyl alcohol (Yield: 85%, chiral purity 99.99% ee).

Example-4: Preparation of L-threo-(2S,3R)-3-(3.4-dihydroxyphenyl)serine (I)

The Droxidopa hydrochloride salt (100 g) was converted to free base by adjusting the pH to 7.5-8.5 of its aqueous solution using triethylamine (150 mL) in methanol (150 mL) as solution. The solid was filtered and washed with water (100 mL) followed by washing with methanol (100 mL) to obtain desired product. (Yield: 65 g (76.5%), chiral purity 99.99% ee).

Example-5: Purification of Preparation of L-threo-(2S,3R)-3-(3.4-dihydroxyphenyl)serine (I) Hydrochloride Charged droxidopa hydrochloride (35 g) in a flask followed by the addition of demineralized water (10 V) and concentrated HCl (0.5 V) (volumes with respect to weight of HCl salt); the reaction mixture was stirred at temperature of about 25-30° C. To the reaction mass was added 0.1% w/w sodium borohydride in 4 V of DM water (with respect toweight of HCl salt) and further continued stirring at temperature of about 25-30° C. for about 30 minutes. The reaction mixture was filtered, treated with activated carbon and passed through hyflo bed. Obtained the pure aqueous solution of L-threo-(2S,3R)-3-(3.4-dihydroxyphenyl)serine (I) hydrochloride with impurity less than 0.06%.

The pure (I) HCl salt was further converted to its free base that is L-threo-(2S,3R)-3-(3.4-dihydroxyphenyl)serine (I) (Droxidopa) using the method disclosed under Example-4.

We claim:

1. A process of preparation of compound (I) or its salt, ;

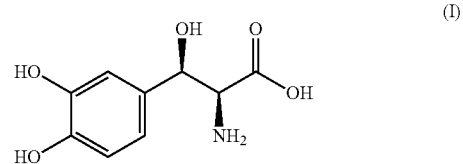 [SMILES: N[C@H](C(=O)O)[C@H](O)c1ccc(O)c(O)c1]

comprising the steps of,
(a) reacting the compound (III) of the following formula,

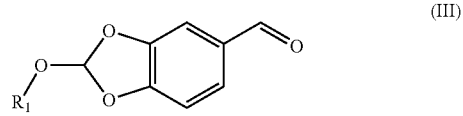

wherein $R_1$ is selected from a group consisting of hydrogen, unsubstituted alkyl, substituted alkyl, cycloalkyl, aryl, heterocyclic and protecting group;
with a metal complex (II) of the following formula,

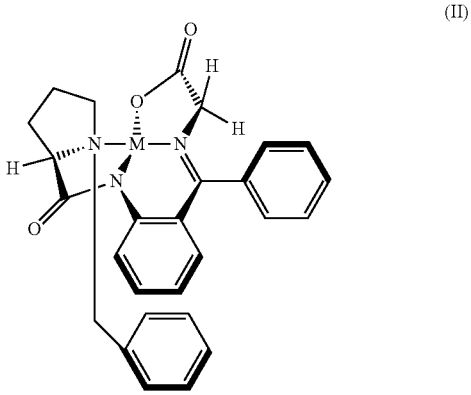

wherein 'M' is a metal selected from $Cu^{2+}$, $Ni^{2+}$, and $Zn^{2+}$,
(b) hydrolyzing of the compound (IV) of the following formula obtained from step (a) in presence of an acid,

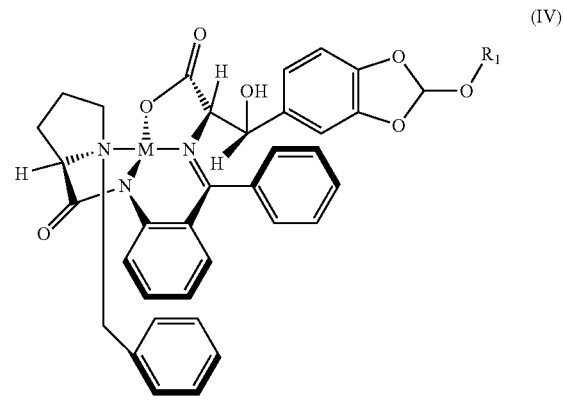

(c) optionally, treating the acid salt of compound (I) of the following formula obtained from step (b) with a base, and

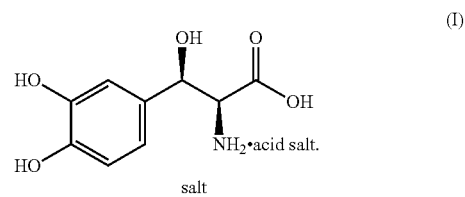

(d) optionally, purifying compound (I) or its salt by treatment with a metal hydride.

2. The process according to claim 1, wherein step (a) is performed in the presence of a metal alkoxide which is selected from the group consisting of sodium methoxide, sodium ethoxide, sodium isopropoxide, potassium methoxide, sodium tertiary butoxide, potassium tertiary butoxide and mixtures thereof.

3. The process according to claim 1, wherein the acid at step (b) is selected from the group consisting of hydrochloric acid, hydrobromic acid, hydrofluoric acid, nitric acid, sulfuric acid , phosphoric acid and mixtures thereof.

4. The process according to claim 1, wherein the base at step (c) is an organic base or an inorganic base; selected from the group consisting of triethylamine (TEA), N,N-diisopropylethylamine, tripropylamine, pyridine, sodium carbonate, sodium bicarbonate, potassium carbonate, sodium hydroxide, potassium hydroxide, lithium hydroxide, lithium carbonate, sodium bicarbonate, potassium bicarbonate, sodium hydride, and mixtures thereof.

5. The process according to claim 1, wherein step (d) for the purification of L-threo-(2S,3R)-3-(3,4-dihydroxyphenyl) serine (I) comprises the steps of;
(p) adding Droxidopa (I) salt to a solvent,
(q) adding a metal hydride to the stirring solution of step (p), and
(r) isolating pure Droxidopa (I) salt or its free base.

6. The process according to claim 5, wherein the metal hydride in step (q) is selected from the group consisting of boron hydride, lithium borohydride, sodium borohydride, potassium borohydride, sodium cyanoborohydride, sodium dialkylamine borohydride, dialkyl aluminum hydride, aluminum hydride, sodium aluminum hydride, lithium aluminum hydride, sodium hydride, potassium hydride, rubidium hydride, cesium hydride and mixtures thereof.

7. The process according to claim 5, wherein the solvent in step (p) is selected from the group consisting of water, halogenated solvent, alcoholic solvent, ether solvent, ketone solvent, aromatic solvent, an aprotic solvent and mixtures thereof.

8. The process according to claim 7 wherein the aprotic solvent is selected from acetonitrile, N,N-dimethyl formamide (DMF), N,N-dimethyl acetamide, dimethyl sulfoxide (DMSO) and N-methylpyrrolidone (NMP) and mixtures thereof.

9. A compound: metal complex (IV) of the following formula;

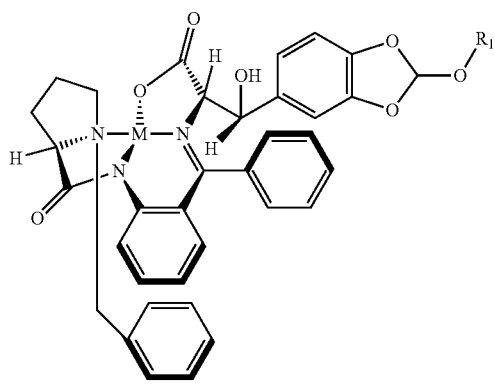

(IV)

wherein 'M' is a metal selected from $Cu^{2+}$, $Ni^{2+}$, and $Zn^{2+}$; and $R_1$ is selected from a group consisting of hydrogen, unsubstituted alkyl, substituted alkyl, cycloalkyl, aryl, heterocyclic and protecting group.

10. The compound according to claim 9, wherein M is $Ni^{2+}$ and $R_1$ is ethyl:
represented as Nickel complex (IVa) of the following formula;

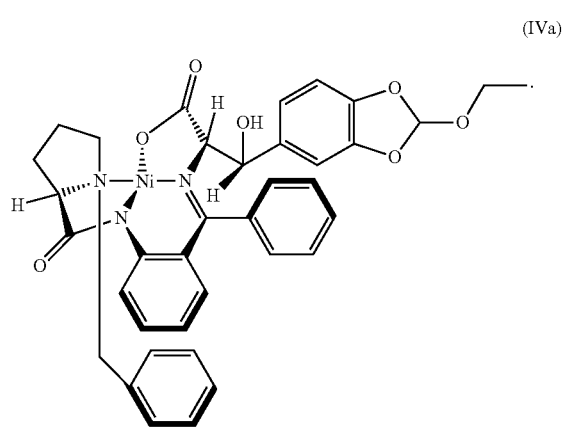

(IVa)

\* \* \* \* \*